United States Patent [19]

Nakazawa

[11] 4,412,987

[45] Nov. 1, 1983

[54] ADDITION AGENT FOR MEDICINES OR COSMETICS

[76] Inventor: Kazuharu Nakazawa, No. 105 Oji-Mansion, 7-8, 3-chome, Harada-dori, Nada-ku, Kobe-shi, Japan

[21] Appl. No.: 305,345

[22] Filed: Sep. 24, 1981

[30] Foreign Application Priority Data

Oct. 15, 1980 [DE] Fed. Rep. of Germany .... 55-144589

[51] Int. Cl.³ ............................................. A61K 35/32
[52] U.S. Cl. ..................................... 424/95; 424/359; 424/360; 424/365
[58] Field of Search .................. 424/95, 359, 360, 365

[56] References Cited

PUBLICATIONS

Harry–Cosmetic Materials, vol. 2 (1950), pp. 133, 134, 169 & 170.
U.S. Dispensatory–25th edit. (1955), pp. 598–600 & 742 & 743.

*Primary Examiner*—Sam Rosen
*Attorney, Agent, or Firm*—Wenderoth, Lind & Ponack

[57] ABSTRACT

This invention relates to an addition agent for medicines or cosmetics obtained by heating the fat and bones of a pig at high temperatures. The addition agent is readily absorbed into the body.

8 Claims, No Drawings

ADDITION AGENT FOR MEDICINES OR COSMETICS

BACKGROUND OF THE INVENTION

This invention relates to an addition agent for medicines or cosmetics, and provides such products as are readily absorbed into the body.

Mineral inorganic compounds or high-molecular compounds have been hitherto used in preparing addition agents for medicines or cosmetics. Although they are satisfactory as extending agents, these addition agents are absorbed into the body with difficulty, and in this respect they need to be much improved and developed.

No matter how excellent the medicinal virtues of a substance may be, it is difficult for the substance to have a good remedial effect if it is not readily absorbed into the body. Thus, when considering the addition agents for medicines or cosmetics, it is very important to consider whether it is readily absorbed into the body.

SUMMARY OF THE INVENTION

An object of the invention is to provide an addition agent for medicines or cosmetics with improved properties.

Another object of the invention is to provide an addition agent for medicines or cosmetics which are readily absorbed into the body.

DETAILED DESCRIPTION OF THE INVENTION

The addition agent of the present invention can be obtained by heating the fats and bones of a pig at high temperatures. The analysis of the ingredients of the addition agent by the Japan Oil Materials Official Approval Association (Corporate Juridical Person), General Analysis Center, is as follows:

| | |
|---|---|
| Tocopherol | 120 mmg/100g |
| Arsenic | 0.1 ppm or below |
| Heavy metal (as Pb) | 2.0 ppm or below |
| Calcium | 6.39 mmg/kg |
| Phosphorus | 52.7 mmg/kg |
| Iodine number | 72.6 |

It is necessary that bones of a pig to be used in this invention be broken up before heating. Most preferably, the bones should be broken up to the size of approximately 3 cm. The fats and the broken up bones of a pig are first heated at a temperature of 700° C. to 1,000° C. for four to five hours and then at a temperature of 1,300° C. to 1,400° C. for one hour to one hour and thirty minutes.

After heating, the resultant hot solution of about 1,300° C. is immediately filtered by gravity to remove a precipitate therefrom, and the filtrate is allowed to stand at room temperature for not less than six hours, to obtain the product of the invention having the above-mentioned analytical values.

Such product having the above-mentioned analytical values has unique properties, and the results of the tests on it show that it has an excellent absorbency when used as an addition agent either for an internal medicine or for an external application.

Thus, when used as an addition agent for medicines, it will improve the remedial value of the medicine; and when used as an addition agent for cosmetics, it will have an excellent cosmetic effect on the surface of the skin because of its high absorbency.

In this connection it can be said that the product of the invention having the above-mentioned analytical values is of course neither toxic in the amount used in a medicine containing it, nor does it hinder the medical value of such medicine.

The raw materials for the product of the invention are available in nature, cheaply and abundantly. This is also one of the advantages of the invention.

When the product of the invention is used as an addition agent for a medicine, 2 to 3 parts by weight of the medicine are blended with 10 parts by weight of the product of the invention. When the product of the invention is used as an addition agent for a cosmetic, 1 to 2 parts by weight of the cosmetic are blended with 10 parts by weight of the product.

Without limiting the invention, the following example is presented to further illustrate the production of the product of the invention.

EXAMPLE

Two kg of bones of a pig which have been previously broken up to approximately 3 cm and one kg of its fats are put into an 18-8 stainless steel pot. They are first heated at 700° C. to 1,000° C. for four hours and thirty minutes, and then at 1,300° C. to 1,400° C. for one hour and thirty minutes.

After heating, a hot solution of about 1,300° C. is filtered by gravity to remove therefrom a brown pulpy precipitate. The light brown filtrate is allowed to cool while standing at room temperature for not less than six hours to obtain one kg of a light brown pulpy product, which is the product of the invention. Such product has the following analytical values.

| | |
|---|---|
| Tocopherol | 120 mmg/100 g |
| Arsenic | 0.1 ppm or below |
| Heavy Metal (as Pb) | 2.0 ppm or below |
| Calcium | 6.39 mmg/kg |
| Phosphorus | 52.7 mmg/kg |
| Iodine number | 72.6 |

The yield of the product is 1 kg.

What is claimed is:

1. An addition agent for medicines and cosmetics obtained by (1) heating fats and bones of a pig in two stages, the first stage being at a temperature of 700° to 1,000° C., and the second stage being at a temperature of 1,300° to 1,400° C., (2) filtering the resultant hot solution to remove precipitates therefrom, and (3) allowing the resultant filtrate to stand at room temperature.

2. The addition agent according to claim 1, wherein the first-stage heating is carried out for four to five hours, and the second-stage heating is carried out for one hour to one hour and thirty minutes.

3. The addition agent according to claim 1, wherein, prior to the heating, the bones are broken up to a size of approximately 3 cm.

4. The addition agent according to claim 1, wherein the filtrate is allowed to stand at room temperature for at least six hours.

5. A process for producing an addition agent for medicines and cosmetics, which comprises (1) heating fats and bones of a pig in two stages, the first stage being at a temperature of 700° to 1,000° C., and the second stage being at a temperature of 1,300° to 1,400° C., (2)

filtering the resultant hot solution to remove precipitates therefrom, and (3) allowing the resultant filtrate to stand at room temperature.

6. The process according to claim 5, wherein the first-stage heating is carried out for four to five hours, and the second-stage heating is carried out for one hour to one hour and thirty minutes.

7. The process according to claim 5, wherein, prior to the heating, the bones are broken up to a size of approximately 3 cm.

8. The process according to claim 5, wherein the filtrate is allowed to stand at room temperature for at least six hours.

* * * * *